(12) United States Patent
Duarte (10) Patent No.: US 8,105,362 B2
(45) Date of Patent: Jan. 31, 2012

(54) PERCUTANEOUS SPINAL ROD INSERTION SYSTEM AND RELATED METHODS

(76) Inventor: Luis E. Duarte, San Angelo, TX (US)

( * ) Notice: Subject to any disclaimer, the term of this patent is extended or adjusted under 35 U.S.C. 154(b) by 225 days.

(21) Appl. No.: 12/493,709

(22) Filed: Jun. 29, 2009

(65) Prior Publication Data

US 2009/0326586 A1 Dec. 31, 2009

Related U.S. Application Data

(60) Provisional application No. 61/076,747, filed on Jun. 30, 2008.

(51) Int. Cl.
*A61B 17/70* (2006.01)
*A61B 17/58* (2006.01)
*A61B 17/88* (2006.01)

(52) U.S. Cl. .................. 606/264; 606/279; 606/301

(58) Field of Classification Search .......... 606/246–279, 606/86 A, 914
See application file for complete search history.

(56) References Cited

U.S. PATENT DOCUMENTS

| | | | |
|---|---|---|---|
| 7,491,218 B2 * | 2/2009 | Landry et al. ................. | 606/246 |
| 7,695,475 B2 * | 4/2010 | Justis et al. ................. | 606/86 A |
| 7,879,039 B2 * | 2/2011 | Perez-Cruet et al. ....... | 606/86 A |
| 7,914,558 B2 * | 3/2011 | Landry et al. ................. | 606/246 |
| 7,931,677 B2 * | 4/2011 | Abdelgany ..................... | 606/279 |
| 2005/0070917 A1 * | 3/2005 | Justis ............................ | 606/104 |
| 2005/0131408 A1 * | 6/2005 | Sicvol et al. ..................... | 606/61 |
| 2005/0171537 A1 * | 8/2005 | Mazel et al. ..................... | 606/61 |
| 2006/0111714 A1 * | 5/2006 | Foley .............................. | 606/61 |
| 2006/0149278 A1 * | 7/2006 | Abdou ........................... | 606/90 |
| 2007/0244473 A1 * | 10/2007 | Thompson et al. ............. | 606/13 |
| 2008/0177269 A1 * | 7/2008 | Seelig ............................ | 606/90 |
| 2008/0255619 A1 * | 10/2008 | Schneiderman et al. ..... | 606/276 |
| 2009/0048601 A1 * | 2/2009 | Forton et al. .................... | 606/64 |
| 2009/0062858 A1 * | 3/2009 | Dziedzic et al. ............. | 606/278 |
| 2009/0228053 A1 * | 9/2009 | Kolb et al. ................. | 606/86 A |
| 2009/0281571 A1 * | 11/2009 | Weaver et al. ................ | 606/246 |

* cited by examiner

*Primary Examiner* — Pedro Philogene
(74) *Attorney, Agent, or Firm* — Allen, Dyer, Doppelt, Milbrath & Gilchrist, P.A.

(57) ABSTRACT

A spinal rod implantation system may be used with pedicle screws to be secured to respective pedicles of a patient's spine, each pedicle screw having a spinal rod channel therethrough. The system may include extenders each including an inner member having a distal end, and an outer member surrounding the inner member and being slidable relative thereto to permit removable coupling of the distal end to a respective pedicle screw. The inner and outer members may include respective features defining a first joint permitting at least partial relative rotation to provide a first degree of rotational freedom. The system may further include extender heads each pivotally coupled to a proximal end of a respective outer member to define a second joint providing a second degree of rotational freedom. A spinal rod insertion assembly may be coupled to the extender heads for guiding the spinal rod through the spinal rod channels.

27 Claims, 9 Drawing Sheets

PERCUTANEOUS SPINAL ROD INSERTION SYSTEM AND RELATED METHODS

RELATED APPLICATION

This application is based upon prior filed provisional application Ser. No. 61/076,747 filed Jun. 30, 2008, the entire subject matter of which is incorporated herein by reference in its entirety.

FIELD OF THE INVENTION

The present invention relates to surgical devices, and, more particularly, to devices for musculoskeletal surgery, such as spinal surgery, and related methods.

BACKGROUND OF THE INVENTION

Spinal implant devices and systems are commonly used to correct or stabilize the position of vertebral segments in a patient's back. Such correction may be necessary as a result of accidents, degenerative diseases, etc.

One exemplary spinal implantation system is the CD Horizon® Sextant™ spinal system from Medtronic, Inc. of Minneapolis, Minn., which allows surgeons to deliver and apply screw and rod implants to the posterior aspect of the spine to promote spinal fusion. As discussed in the fact sheet for the Sextant™ system available at http://wwwp.medtronic.com/Newsroom/LinkedItemDetails.do?itemId=1101756222541&itemType=fact_sheet&lang=en_US:

"The CD HORIZON SEXTANT Spinal System is an implant system composed of rods, screws, specially designed surgical tools and a novel mechanical implant delivery device. This device looks much like the sextant of naval navigation, and is the navigation and insertion tool that allows screws and rods to be applied to the spine in a minimally invasive manner.

Two principal elements comprise this device. The first are screw extenders, which are long metal shafts used to deliver and attach screws to the vertebrae through small skin incisions. These extenders protrude outside of the body, allowing the surgeon to arrange and join their ends so that the second principal part, the rod inserter, may be attached. The rod inserter is an arc-shaped arm that swings on an axis and delivers a pre-cut rod through the skin and muscle and into the heads of the implanted screws."

Despite the advantages of the Sextant™ system, in some cases it may be difficult for the surgeon to properly align the end of the curved arm of the rod inserter with the screw heads. If the surgeon is ultimately unable to make the proper alignment after repeated attempts, the surgeon has to resort to a traditional surgical approach, which is more invasive to the patient. As a result, the patient is required to be under anesthesia for a longer duration, leading to increased risk of complications and a more difficult recovery.

SUMMARY OF THE INVENTION

It is therefore an object of the present invention to provide a spinal rod implantation system and related methods which allows a surgeon enhanced flexibility when positioning a spinal rod.

This and other objects, features, and advantages are provided by a spinal rod implantation system to be used with a plurality of pedicle screws to be secured to respective pedicles of a patient's spine, with each pedicle screw having a spinal rod channel therethrough. The spinal rod implantation system may include a plurality of extenders, each including an inner member having a distal end, and an outer member surrounding the inner member and being slidable relative thereto to permit removable coupling of the distal end of the inner member to a respective pedicle screw. The inner member and the outer member may include respective features defining a first joint permitting at least partial relative rotation to provide a first degree of rotational freedom. The system may further include a plurality of extender heads each pivotally coupled to a proximal end of a respective outer member to define a second joint providing a second degree of rotational freedom. Additionally, a spinal rod insertion assembly may be coupled to the plurality of extender heads for guiding the spinal rod through the spinal rod channels of the plurality of pedicle screws. As such, the spinal rod implantation advantageously provides two degrees of rotational freedom for the surgeon, allowing the surgeon enhanced flexibility in aligning the spinal rod with the screws.

By way of example, the first joint may comprise a tongue and groove joint, and the second joint may comprise a hinge joint. In some embodiments where both degrees of rotational freedom are not required, only the first joint or the second joint need be used.

In addition, the inner members may advantageously be telescopic for adjusting a height of the extender. In accordance with one exemplary embodiment, the spinal rod insertion assembly may include an arcuate guide tube for guiding the spinal rod through the spinal rod channels of the pedicle screws, and at least one alignment member coupling the arcuate guide tube to the extender heads. More particularly, the extender heads may have a respective alignment slot on opposing sides thereof, and the at least one alignment member may comprise a respective alignment member positioned in the alignment slots on the opposing sides of the extender heads. Furthermore, an alignment member handle may connect the alignment members. A spinal rod insertion probe may also be included for directing the spinal rod through the arcuate guide tube and the spinal rod channels of the pedicle screws. Additionally, a reduction clamp assembly may be coupled to the extender heads for aligning the alignment slots.

In accordance with another exemplary embodiment, the spinal rod insertion assembly may include a base pivotally coupled to at least one of the extender heads, and an insertion arm carried by the base for guiding the spinal rod through the spinal rod channels of the pedicle screws. Moreover, the insertion arm may have an arcuate shape.

A related method for implanting a spinal rod is also provided. The method may include providing a plurality of extenders each comprising an inner member having a distal end and an outer member, and positioning the outer members surrounding the inner members so that the outer members are slidable relative to the inner members to permit removable coupling of the distal ends of the inner members to respective pedicle screws. The inner member and the outer member may comprise respective features defining a first joint permitting at least partial relative rotation to provide a first degree of rotational freedom. The method may further include pivotally coupling a plurality of extender heads to a proximal end of a respective outer member to define a second joint providing a second degree of rotational freedom, and coupling a spinal rod insertion assembly to the plurality of extender heads for guiding the spinal rod through the spinal rod channels of the plurality of pedicle screws.

DESCRIPTION OF THE PREFERRED EMBODIMENTS

The present description is made with reference to the accompanying drawings, in which preferred embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime notation is used to indicate similar elements in alternative embodiments.

Referring now to FIGS. 1-9B, a spinal rod insertion system 30 illustratively includes pedicle screws 31, each including a threaded shaft 32 and a pedicle screw head 33 carried by the shaft. Each pedicle screw head 33 has a spinal rod channel or passageway 34 therethrough (see FIG. 8) for receiving a spinal rod 35 therein, which is secured to the pedicle screw head. The spinal rod 35 thus interconnects the pedicle screw heads 33, and the pedicle screws 31 and spinal rod remain in the patient after the surgical procedure is completed, as will be appreciated by those skilled in the art.

Various techniques for inserting pedicle or vertebral screws into a vertebra 40 (FIG. 2) are known. By way of reference, the vertebra 40 illustratively includes a vertebral body 41, pedicles 42 through which the threaded shafts 32 are inserted, and a spinous process 43. One such approach for inserting pedicle screws is through the use of a guide wire, as will be appreciated by those skilled in the art. However, other suitable approaches that will also be appreciated by those skilled in the art may be used as well.

The system 30 further illustratively includes a respective extender 36 for each of the pedicle screws 31, which is attached to the pedicle screw head 33 and extends vertically upward therefrom. That is, the extenders 36 extend from the vertebra 40 out of the patient's back so that the top or proximal end of the extender is a desired distance away from the back to allow sufficient room for a rod insertion tube to move or swing back and forth from the pedicle screw heads. By way of example, the extenders 36 may have a height of about 4-6 inches, although other lengths may also be used. Additionally, each extender 36 illustratively includes an inner member 44 (e.g., a sleeve or partial sleeve) and an outer member 45 (e.g., sleeve) (see FIG. 8). Typically, the inner member 44 has a distal end that is inserted over a pedicle screw head 33, and then when the outer member 45 is pushed down over the inner member it causes the inner member to contract around the pedicle screw head and be secured thereto. That is, the outer member 45 is slidable relative to the inner member 44 to permit removable coupling of the distal end of the inner member to a respective pedicle screw head 33.

Figure 9A:
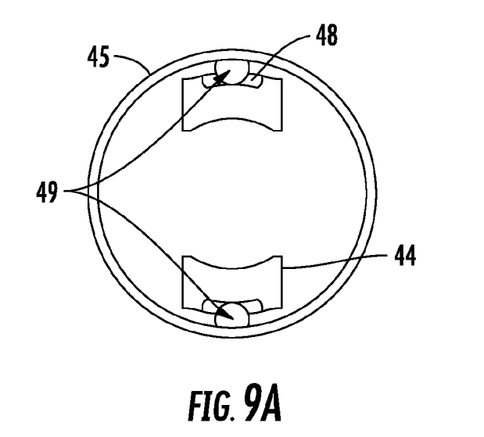
FIG. 9A is a cross-sectional view of the extender of FIG. 8 taken along line A-A.
Figure 9B:
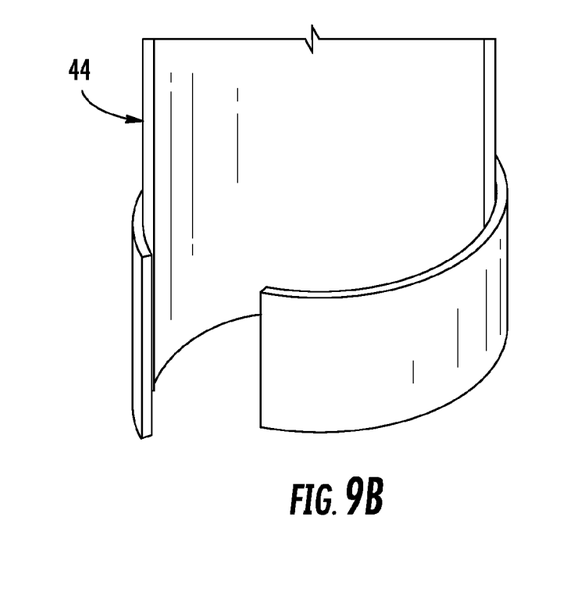
FIG. 9B is an exploded perspective view of the region B of the inner sleeve of the extender of FIG. 8.

In the embodiment illustrated in FIG. 9A, the inner member 44 and the outer member 45 include respective features defining a first joint permitting at least partial relative rotation to provide a first degree of rotational freedom. In particular, the inner member 44 has grooves or slots 48 on opposing outer walls thereof for receiving respective rounded tongues 49 carried on opposing inner walls of the outer members 45. In the exemplary embodiment, the grooves 48 are wider than the tongues 49, which allows the tongues a degree of movement to pivot or rotate around a center axis of the outer sleeve 45, thereby providing the first degree of rotational freedom, and therefore providing the surgeon with enhanced flexibility in aligning and moving the extenders 36. Moreover, the inner members 44 may also be telescopic so that each side thereof can slide up and down independently, thereby allowing multi-axial pedicle screw head 33 movement as well, as illustrated in FIG. 9B.

Respective extender heads 46 are carried on top of the outer member 45. Each extender head 46 is pivotally coupled to a proximal end of a respective outer member 45 to define a second joint providing a second degree of rotational freedom. In the illustrated example, a through bolt or pin 59 connects the extender heads 46 to their respective outer members 45 to thereby define a hinge joint therewith, thus providing the second degree of rotational freedom. In some embodiments where both degrees of rotational freedom are not required, only the first joint or the second joint need be used.

Figure 1:
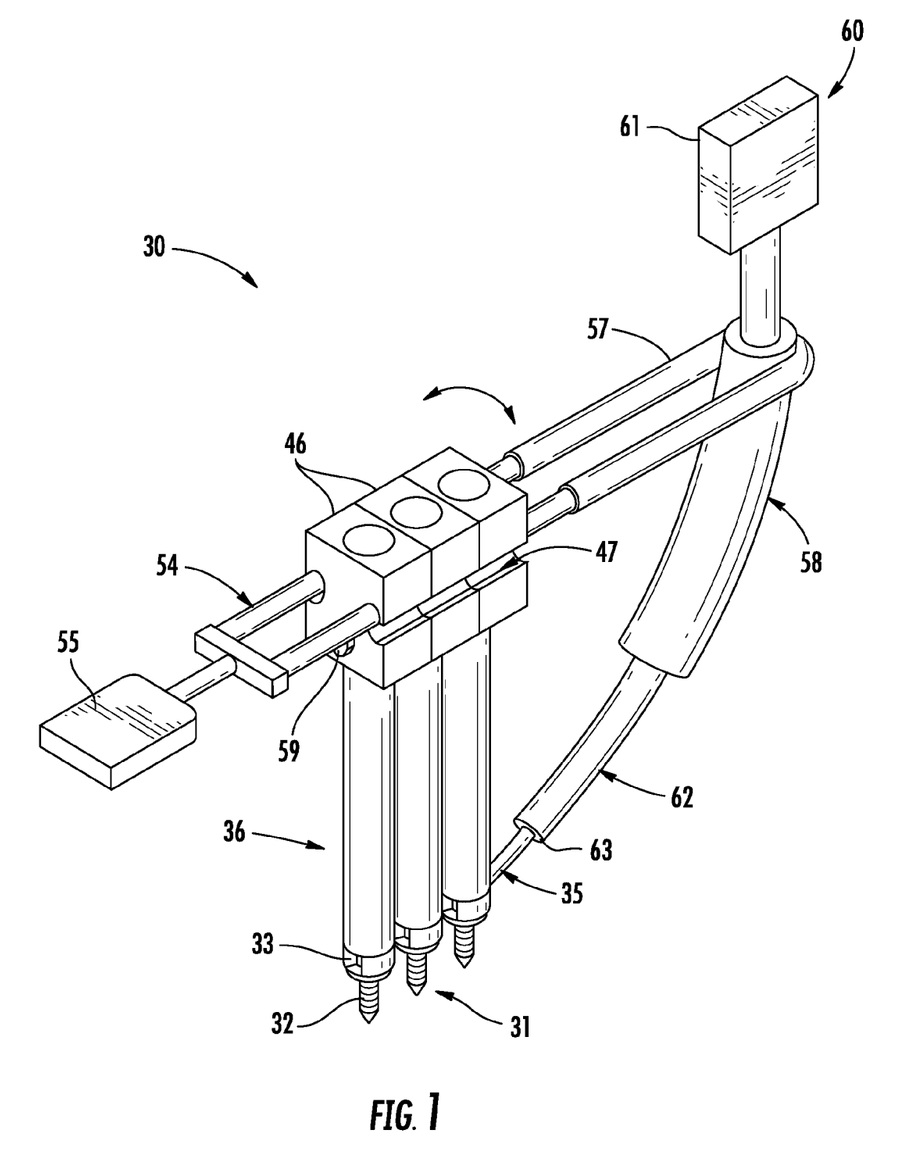
FIG. 1 is a perspective view of a spinal rod insertion system in accordance with one embodiment of the invention.
Figure 2:
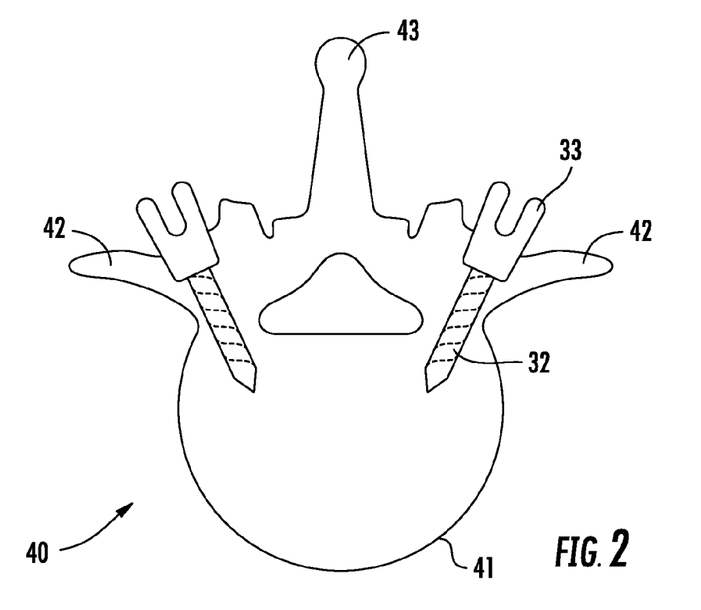
FIG. 2 is a top view of a vertebra and illustrating placement of the pedicle screws of the system of FIG. 1 therein.
Figure 3:
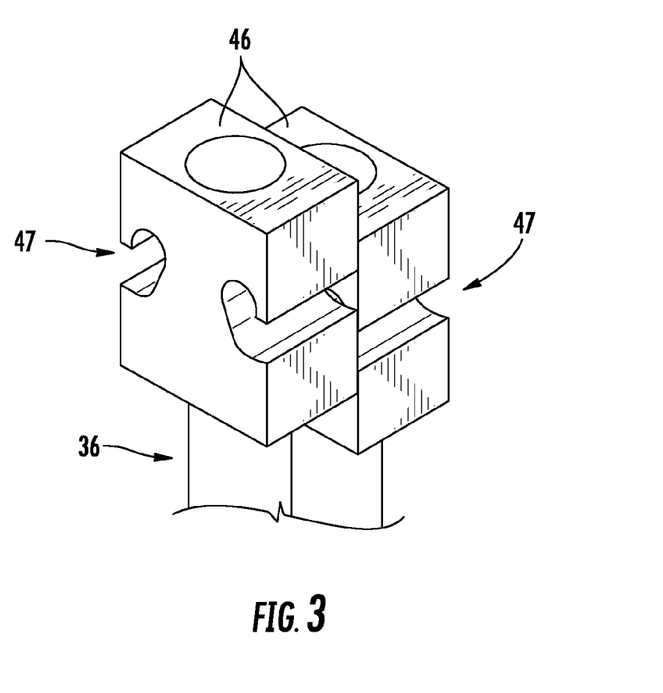
FIG. 3 is a perspective view of the extender heads of the system of FIG. 1 prior to alignment and connection thereof.
Figure 4:
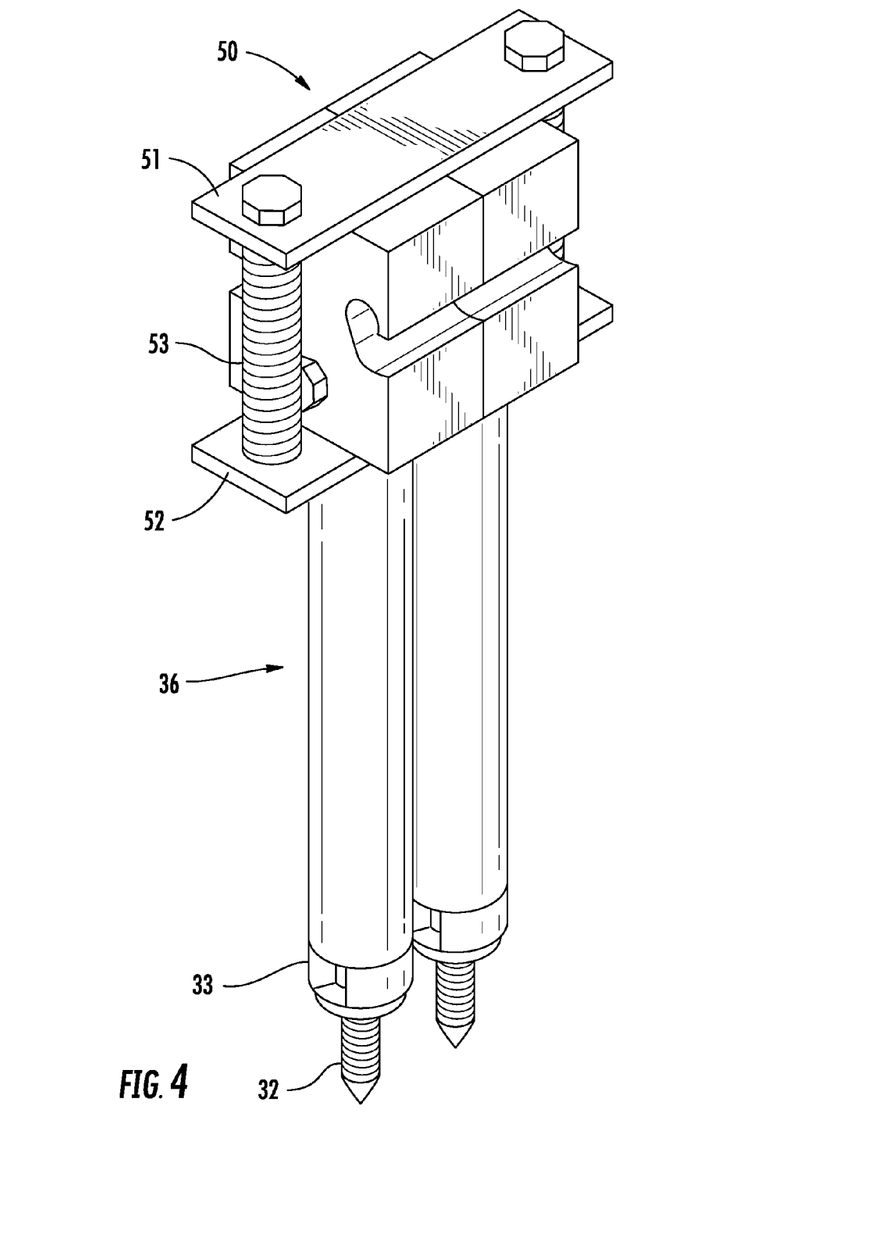
FIG. 4 is a perspective view of the pedicle screws, extenders, and extender heads of the system of FIG. 1 with a reduction clamp on the extender heads for alignment thereof.
Figure 5:
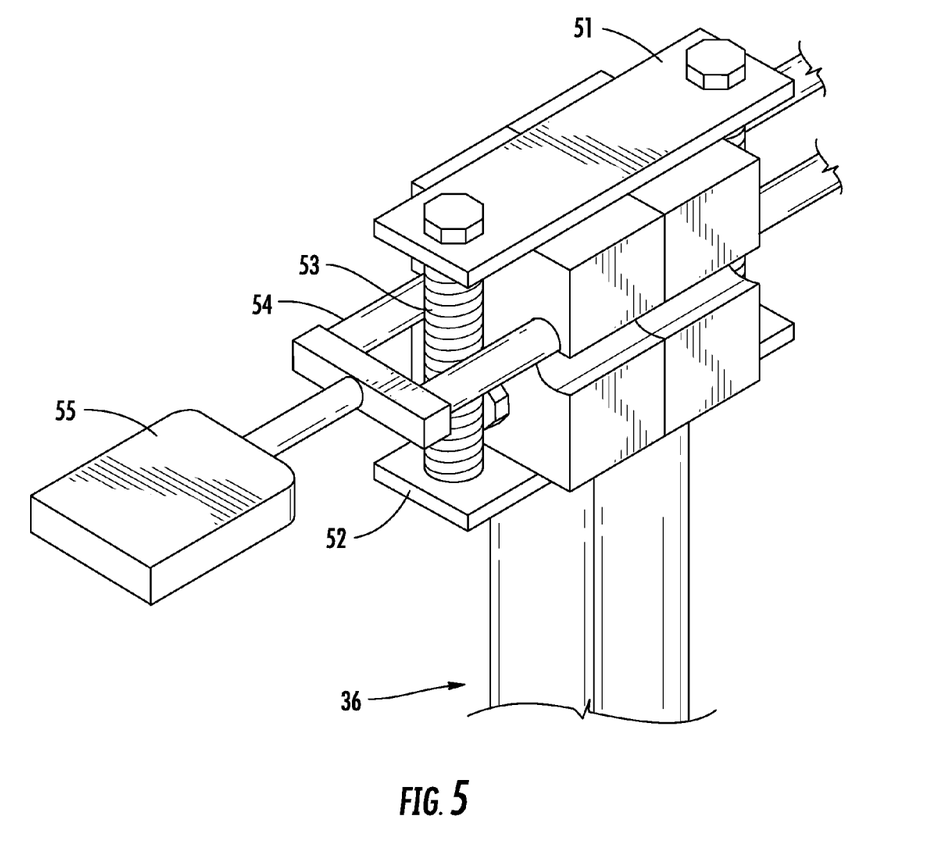
FIG. 5 is a perspective view of the extender heads and reduction clamp of FIG. 4 after alignment thereof and insertion of alignment members.
Figure 6:
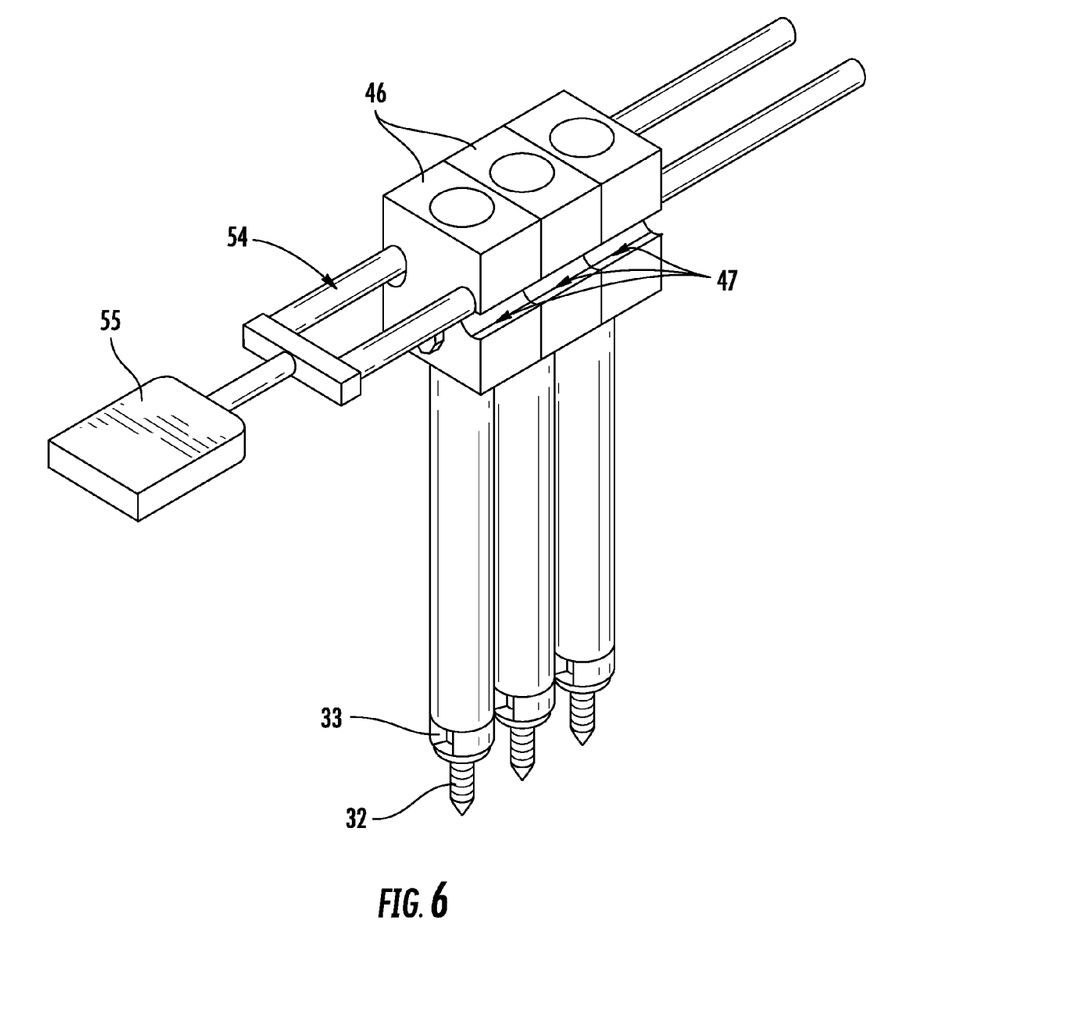
FIG. 6 is a perspective view of the pedicle screws, extenders, and extender heads of FIG. 5 after removal of the reduction clamp.
Figure 7:
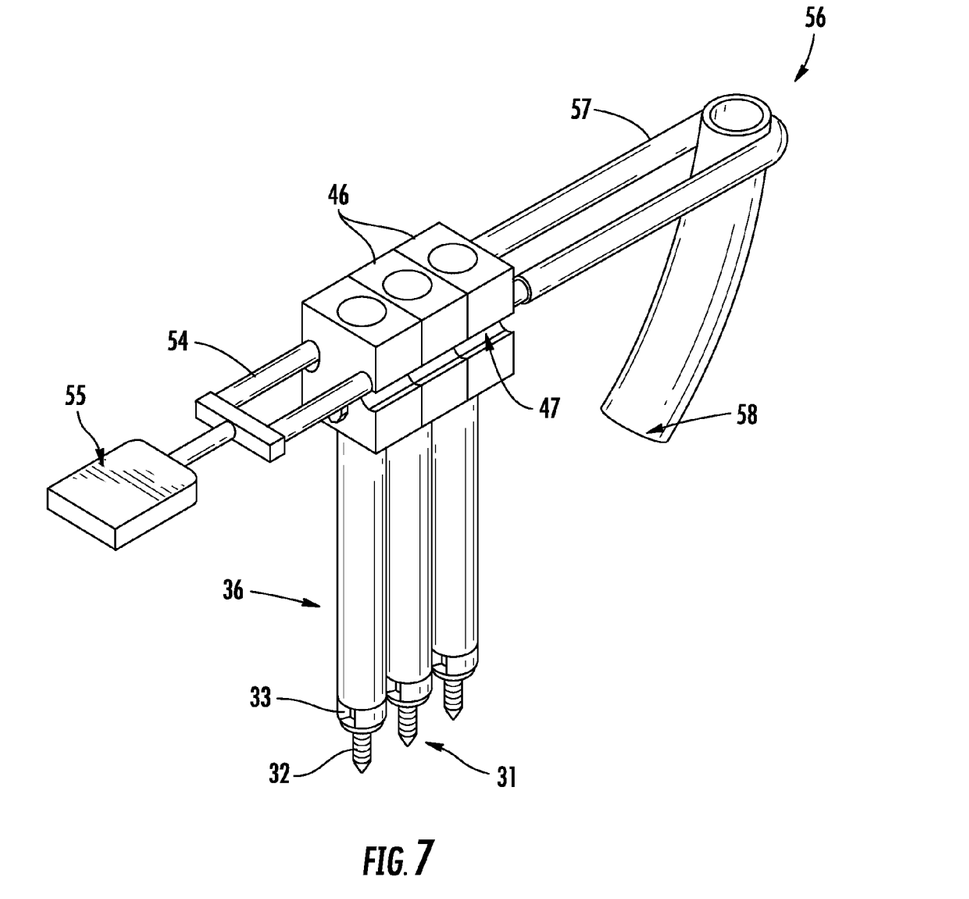
FIG. 7 is a perspective view of the pedicle screws, extenders, and extender heads of FIG. 6 after mounting of a rod insertion tube on the alignment members.
Figure 8:
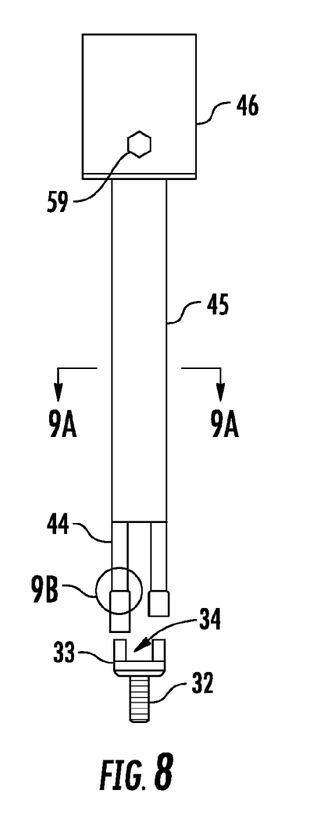
FIG. 8 is a side view of an extender of the system of FIG. 1 being positioned on a pedicle screw.

As seen in FIG. 3, the extender heads 46 have alignment slots 47 therein which may not initially be aligned due to lateral offset between vertebrae, depth of threaded shaft 32 insertion, etc. As such, to bring the alignment slots 47 of the different extender heads 46 into alignment, a reduction clamp assembly 50 may optionally be used. The reduction clamp assembly illustratively includes a top plate 51 to be positioned on the top of the extender heads 46, a bottom plate 52 to be positioned on the bottom of the extender heads, and biasing screws 53 for biasing the top and bottom plates toward one another to thereby align the extender heads and alignment slots 47. In some embodiments, other devices or tools may be used for aligning the slots 47, as will be appreciated by those skilled in the art.

Once aligned, alignment members 54 (tubes in the illustrated example) are inserted in the alignment slots 47 of each extender head 46, one on each side of the extender heads. A handle 55 connects the two alignment members 54, and allows the alignment members to be moved along an axis generally parallel to the patient's spine. The handle 55 may be a separate piece which is connected to the alignment members 54 after they are positioned in the alignment slots 47, or the handle and alignment members may be a single piece/monolithic unit in other embodiments. The extender heads 46 are pivotally mounted on the extenders 36 by the through bolt 59, which allows the surgeon to rotate the extender heads about an axis parallel to the axis of the spine (as represented by the curved two-headed arrow in FIG. 1), which provides a greater degree of freedom in aligning the spinal rod 35 with the passageways 34.

A rod insertion assembly 56 may then be mounted on the alignment members 54, which is used for guiding the spinal rod 35 into the passageways 34 of the pedicle screw heads 33. More particularly, in the illustrated embodiment the rod insertion assembly 56 includes a pair of arms 57 each of which slidably engages a respective alignment member 54, and an arcuate guide tube 58 carried by the arms which points down and in toward the pedicle screws 31. Different configurations may be possible in different embodiments. For example, the arms 57 need not be slidable on the alignment members 54 (e.g., they could be clamped, etc.), and they could be directly carried by the extender heads 46 rather than the alignment members.

The rod insertion assembly 56 may advantageously be securely attached to the extender heads 46 (via the alignment members 54 in the illustrated embodiment) so that it can not only pivot with the extender heads, but also provide a stable support for guiding the spinal rod 35 into the passageways 34. To this end, a rod insertion probe 60 illustratively includes a probe handle 61 and an insertion member 62 coupled to the probe handle. In the present embodiment, the insertion member 62 is a flexible tube that is inserted through the arcuate guide tube 58 and has an end 63 configured to hold the spinal rod 35 while it is being inserted through the passageways 34 of the pedicle screw heads 33. Once the spinal rod 35 is in place, the surgeon uses the probe handle 61 to withdraw the insertion member 62 from the arcuate guide tube 58, leaving the spinal rod in place in the passageways 34, as will be appreciated by those skilled in the art. It should be noted that while the handle 55, extender heads 46, and probe handle 61 are shown as generally rectangular in the illustrated embodiment, other suitable geometric shapes may also be used in other embodiments, as will be appreciated by those skilled in the art.

The spinal rod insertion system 30 advantageously provides a minimally invasive approach for spinal rod insertion that helps avoid the muscle stripping and retraction associated with traditional spinal rod insertion surgery, to therefore reduce back pain and potential scarring and damage to the muscles. Yet, as a result of the lateral degree of freedom along the axis of the patient's spine from the slidable alignment members 54 and arms 57, as well as the rotational movement of the extender heads 46 about the axis of the spine (i.e., the first and second degrees of rotational freedom), surgeons are more readily able to position the system for aligning the spinal rod 35 within the passageways 34 of the pedicle screw heads 33. As a result, the likelihood that the surgeon can complete the rod insertion procedure without having to result to the traditional and more traumatic approach is increased. Stated alternatively, the spinal rod insertion system 30 allows for percutaneous rod placement while advantageously providing polyaxial movement to assist the surgeon, as will be appreciated by those skilled in the art.

Figure 10:
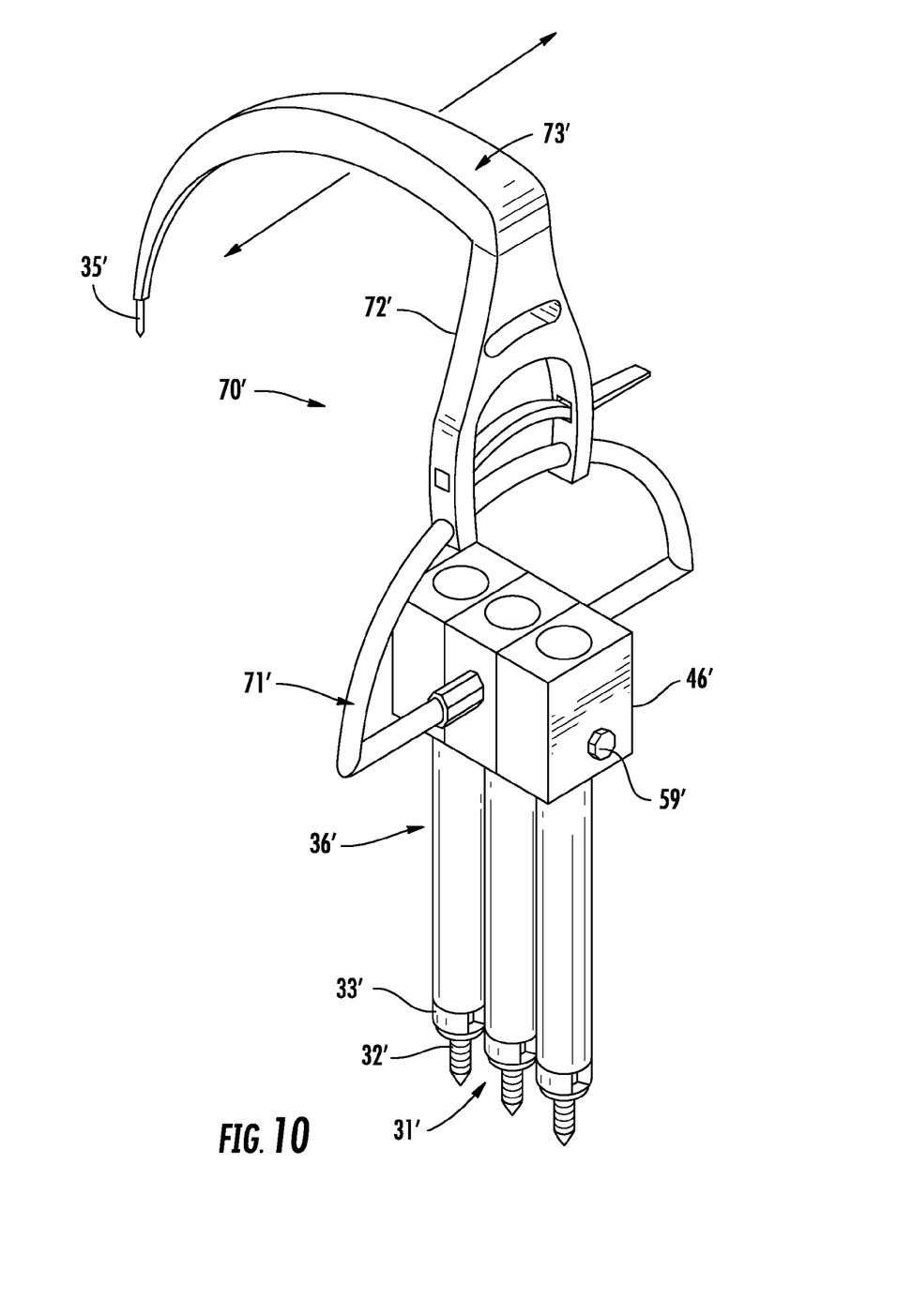
FIG. 10 is a perspective view of an alternative embodiment of a spinal rod insertion system in accordance with the invention.
Figure 11:
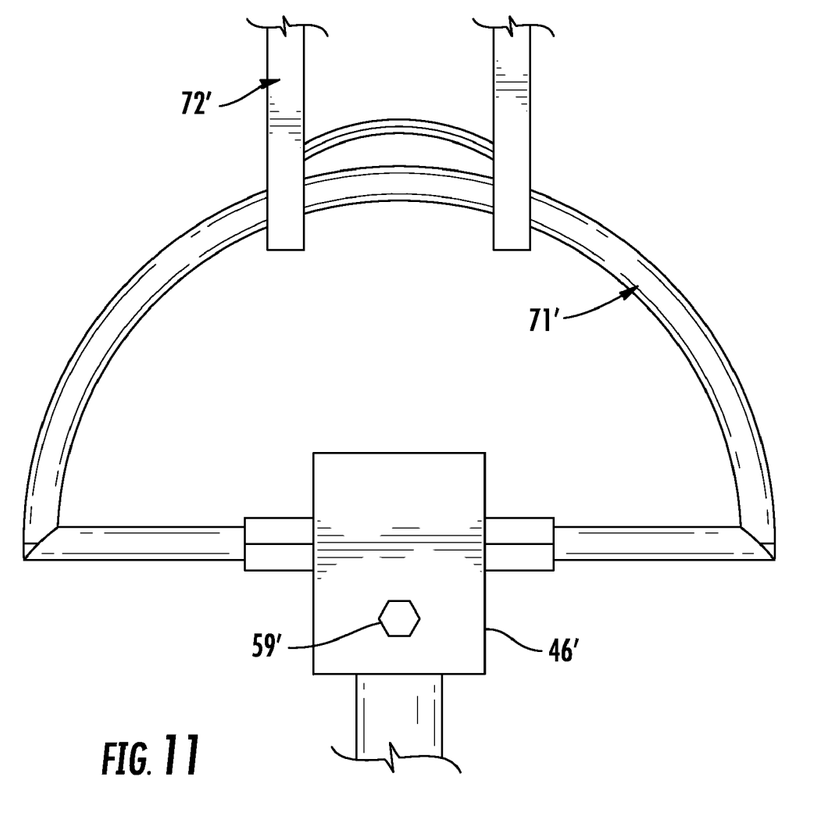
FIG. 11 is a side view of the support arc of the spinal rod insertion system of FIG. 10.

Turning to FIGS. 10 and 11, another exemplary spinal rod insertion system 30' is now described. This illustrated embodiment is similar to the one described above in that it includes pedicle screws 31', extenders 36', and extender heads 46'. However, in the present example a rod insertion assembly 70' includes a support arc 71' connected to opposing sides of the middle extender head 46' as shown, although it could be connected to other extender heads in different embodiments. A pivotal base 72' is movable laterally from side to side of the support arc 71', and also pivots about the support arc to swing down toward the pedicle screw heads 33' and back. A rod insertion member or arm 73' (here an arc) is carried by the pivotal base 72' and is manipulated by the surgeon to insert the spinal rod 35' into the passageways 34' of the pedicle screw heads 33', as discussed above. Here again, because of the advantageous configuration, the surgeon is thereby permitted to extend the rod insertion assembly 70' longitudinally along the length of the patient's spine, as well as rotate the pivotal base 72' and insertion member 73' to advantageously achieve the appropriate angle for insertion of the spinal rod 35' with a higher degree of accuracy.

Many modifications and other embodiments of the invention will come to the mind of one skilled in the art having the benefit of the teachings presented herein. Therefore, it is understood that the invention is not to be limited to the specific exemplary embodiments disclosed herein.

That which is claimed is:

1. A spinal rod implantation system to be used with a plurality of pedicle screws to be secured to respective pedicles of a patient's spine, each pedicle screw having a spinal rod channel therethrough, the spinal rod implantation system comprising:
    a plurality of extenders, each comprising
        an inner member having a distal end, and
        an outer member surrounding said inner member and being slidable relative thereto to permit removable coupling of the distal end of said inner member to a respective pedicle screw,
        said inner member and said outer member comprising respective features defining a first joint permitting at least partial relative rotation to provide a first degree of rotational freedom;
    a plurality of extender heads, each pivotally coupled to a proximal end of a respective outer member to define a second joint providing a second degree of rotational freedom; and
    a spinal rod insertion assembly coupled to said plurality of extender heads for guiding the spinal rod through the spinal rod channels of the plurality of pedicle screws.

2. The spinal rod implantation system of claim 1 wherein the first joint comprises a tongue and groove joint.

3. The spinal rod implantation system of claim 1 wherein the second joint comprises a hinge joint.

4. The spinal rod implantation system of claim 1 wherein said inner members are telescopic for adjusting a height of said extender.

5. The spinal rod implantation system of claim 1 wherein said spinal rod insertion assembly comprises:
    an arcuate guide tube for guiding the spinal rod through the spinal rod channels of the pedicle screws; and
    at least one alignment member coupling said arcuate guide tube to said extender heads.

6. The spinal rod implantation system of claim 5 wherein said extender heads have a respective alignment slot on opposing sides thereof; and wherein said at least one alignment member comprises a respective alignment member positioned in the alignment slots on the opposing sides of said extender heads.

7. The spinal rod implantation system of claim 6 further comprising a reduction clamp assembly to be coupled to said extender heads for aligning the alignment slots.

8. The spinal rod implantation system of claim 6 further comprising an alignment member handle connecting said alignment members.

9. The spinal rod implantation system of claim 5 further comprising a spinal rod insertion probe for directing the spinal rod through said arcuate guide tube and the spinal rod channels of the pedicle screws.

10. The spinal rod implantation system of claim 1 wherein said spinal rod insertion assembly comprises:
   a base pivotally coupled to at least one of said extender heads; and
   an insertion arm carried by said base for guiding the spinal rod through the spinal rod channels of said pedicle screws.

11. The spinal rod implantation system of claim 10 wherein said insertion arm has an arcuate shape.

12. A spinal rod implantation system to be used with a plurality of pedicle screws to be secured to respective pedicles of a patient's spine, each pedicle screw having a spinal rod channel therethrough, the spinal rod implantation system comprising:
   a plurality of extenders, each comprising
      an inner member having a distal end, and
      an outer member surrounding said inner member and being slidable relative thereto to permit removable coupling of the distal end of said inner member to a respective pedicle screw,
      said inner member and said outer member comprising respective features defining a joint permitting at least partial relative rotation to provide a degree of rotational freedom;
   a plurality of extender heads each coupled to a proximal end of a respective outer member; and
   a spinal rod insertion assembly coupled to said plurality of extender heads for guiding the spinal rod through the spinal rod channels of the plurality of pedicle screws.

13. The spinal rod implantation system of claim 12 wherein the joint comprises a tongue and groove joint.

14. The spinal rod implantation system of claim 12 wherein said inner members are telescopic for adjusting a height of said extender.

15. A spinal rod implantation system to be used with a plurality of pedicle screws to be secured to respective pedicles of a patient's spine, each pedicle screw having a spinal rod channel therethrough, the spinal rod implantation system comprising:
   a plurality of extenders, each comprising
      an inner member having a distal end, and
      an outer member surrounding said inner member and being slidable relative thereto to permit removable coupling of the distal end of said inner member to a respective pedicle screw;
   a plurality of extender heads, each pivotally coupled to a proximal end of a respective outer member to define a joint providing a degree of rotational freedom; and
   a spinal rod insertion assembly coupled to said plurality of extender heads for guiding the spinal rod through the spinal rod channels of the plurality of pedicle screws.

16. The spinal rod implantation system of claim 15 wherein the joint comprises a hinge joint.

17. The spinal rod implantation system of claim 15 wherein said inner members are telescopic for adjusting a height of said extender.

18. A method for implanting a spinal rod with a plurality of pedicle screws to be secured to respective pedicles of a patient's spine, each pedicle screw having a spinal rod channel therethrough, the method comprising:
   providing a plurality of extenders each comprising an inner member having a distal end and an outer member;
   positioning the outer members surrounding the inner members so that the outer members are slidable relative to the inner members to permit removable coupling of the distal ends of the inner members to respective pedicle screws, the inner member and the outer member comprising respective features defining a first joint permitting at least partial relative rotation to provide a first degree of rotational freedom;
   pivotally coupling a plurality of extender heads to a proximal end of a respective outer member to define a second joint providing a second degree of rotational freedom; and
   coupling a spinal rod insertion assembly to the plurality of extender heads for guiding the spinal rod through the spinal rod channels of the plurality of pedicle screws.

19. The method of claim 18 wherein the first joint comprises a tongue and groove joint.

20. The method of claim 18 wherein the second joint comprises a hinge joint.

21. The method of claim 18 wherein the inner members are telescopic for adjusting a height of the extender.

22. A method for implanting a spinal rod with a plurality of pedicle screws to be secured to respective pedicles of a patient's spine, each pedicle screw having a spinal rod channel therethrough, the method comprising:
   providing a plurality of extenders each comprising an inner member having a distal end and an outer member;
   positioning the outer members surrounding the inner members so that the outer members are slidable relative to the inner members to permit removable coupling of the distal ends of the inner members to respective pedicle screws, the inner member and the outer member comprising respective features defining a joint permitting at least partial relative rotation to provide a degree of rotational freedom;
   coupling a plurality of extender heads to a proximal end of a respective outer member; and
   coupling a spinal rod insertion assembly to the plurality of extender heads for guiding the spinal rod through the spinal rod channels of the plurality of pedicle screws.

23. The method of claim 22 wherein the joint comprises a tongue and groove joint.

24. The method of claim 22 wherein the inner members are telescopic for adjusting a height of the extender.

25. A method for implanting a spinal rod with a plurality of pedicle screws to be secured to respective pedicles of a patient's spine, each pedicle screw having a spinal rod channel therethrough, the method comprising:
   providing a plurality of extenders each comprising an inner member having a distal end and an outer member;
   positioning the outer members surrounding the inner members so that the outer members are slidable relative to the inner members to permit removable coupling of the distal end of the inner member to a respective pedicle screw;
   pivotally coupling a plurality of extender heads to a proximal end of a respective outer member to define a joint providing a degree of rotational freedom; and
   coupling a spinal rod insertion assembly to the plurality of extender heads for guiding the spinal rod through the spinal rod channels of the plurality of pedicle screws.

26. The method of claim 25 wherein the joint comprises a hinge joint.

27. The method of claim 25 wherein the inner members are telescopic for adjusting a height of the extender.

* * * * *